(12) United States Patent
Wack et al.

(10) Patent No.: US 9,872,783 B2
(45) Date of Patent: Jan. 23, 2018

(54) STENT

(71) Applicant: C. R. Bard, Inc., Murray Hill, NJ (US)

(72) Inventors: Thilo Wack, Durmersheim (DE); Thomas Haas, Karlsruhe (DE)

(73) Assignee: C. R. Bard, Inc., Tempe, AZ (US)

( * ) Notice: Subject to any disclaimer, the term of this patent is extended or adjusted under 35 U.S.C. 154(b) by 0 days.

(21) Appl. No.: 14/793,648

(22) Filed: Jul. 7, 2015

(65) Prior Publication Data
US 2015/0313734 A1 Nov. 5, 2015

Related U.S. Application Data

(60) Continuation of application No. 14/045,603, filed on Oct. 3, 2013, now Pat. No. 9,084,691, which is a division of application No. 12/514,177, filed as application No. PCT/EP2007/062155 on Nov. 9, 2007, now Pat. No. 8,551,156.

(30) Foreign Application Priority Data

Nov. 10, 2006 (GB) .................................. 0622465.3

(51) Int. Cl.
*A61F 2/89* (2013.01)
*A61F 2/86* (2013.01)
*B23K 26/38* (2014.01)
*A61F 2/915* (2013.01)

(52) U.S. Cl.
CPC ................ *A61F 2/86* (2013.01); *A61F 2/915* (2013.01); *B23K 26/38* (2013.01); *A61F 2002/91541* (2013.01); *A61F 2002/91558* (2013.01); *A61F 2230/0054* (2013.01); *A61F 2230/0069* (2013.01); *A61F 2240/002* (2013.01); *A61F 2250/0036* (2013.01)

(58) Field of Classification Search
CPC .... A61F 2/82; A61F 2/91; A61F 2/915; A61F 2240/001; A61F 2002/915141; A61F 2002/91558; B23K 26/38; B23K 15/08; B23K 26/08–26/0892; B23K 26/035
USPC .............. 219/121.68, 121.69; 623/1.11–1.54
See application file for complete search history.

(56) References Cited

U.S. PATENT DOCUMENTS

| | | | | |
|---|---|---|---|---|
| 3,749,878 A * | 7/1973 | Sullivan | ................. | B23K 26/10 219/121.67 |
| 3,943,324 A * | 3/1976 | Haggerty | ............... | C04B 35/653 117/217 |
| 5,345,057 A * | 9/1994 | Muller | ................. | B23K 26/142 219/121.71 |
| 5,780,807 A * | 7/1998 | Saunders | ................. | A61F 2/91 219/121.71 |
| 5,824,059 A * | 10/1998 | Wijay | ..................... | A61F 2/90 623/1.15 |

(Continued)

*Primary Examiner* — Kathleen Holwerda

(57) ABSTRACT

A radially expansible annular stent is disclosed. The stent comprises a plurality of stenting turns around a lumen centred on a longitudinal axis. Adjacent turns of the stent are joined by connector struts. The stent annulus has a wall thickness related to the material from which it is formed. The radial thickness of the connector struts is smaller than that of the stent annulus. A method of making such a stent is also disclosed. The method includes cutting the connector struts from a tubular workpiece with a laser beam. The laser beam is aimed so as to be offset from a longitudinal axis of the workpiece to provide the reduced radial thickness of the connector struts.

5 Claims, 2 Drawing Sheets

(56) References Cited

U.S. PATENT DOCUMENTS

| | | | | |
|---|---|---|---|---|
| 6,605,110 B2* | 8/2003 | Harrison | .................... | A61F 2/91 |
| | | | | 623/1.15 |
| 6,629,994 B2* | 10/2003 | Gomez | .................... | A61F 2/91 |
| | | | | 623/1.15 |
| 6,652,572 B2* | 11/2003 | Kugler | ..................... | A61F 2/07 |
| | | | | 623/1.13 |
| 2002/0198589 A1* | 12/2002 | Leong | ....................... | A61F 2/91 |
| | | | | 623/1.15 |
| 2006/0054604 A1* | 3/2006 | Saunders | ............... | B23K 26/08 |
| | | | | 219/121.69 |
| 2006/0064153 A1* | 3/2006 | Langhans | ................. | A61F 2/91 |
| | | | | 623/1.15 |

* cited by examiner

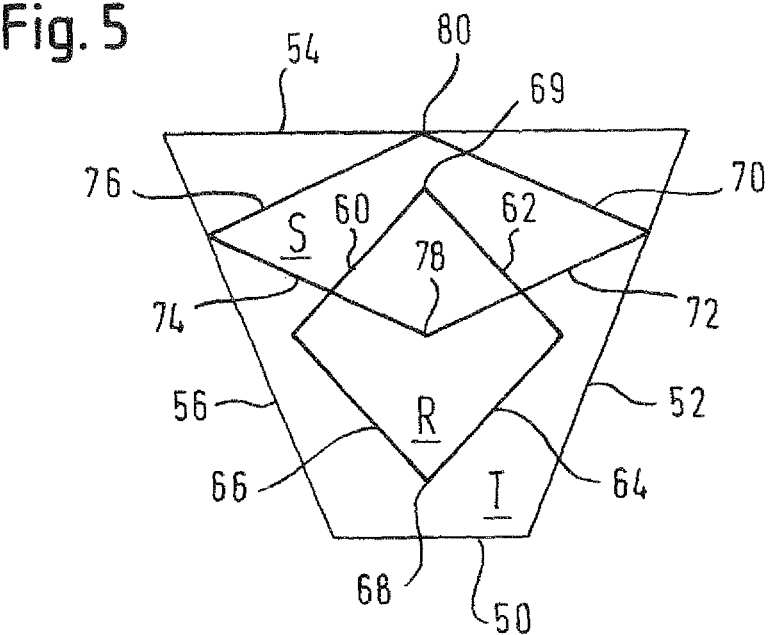
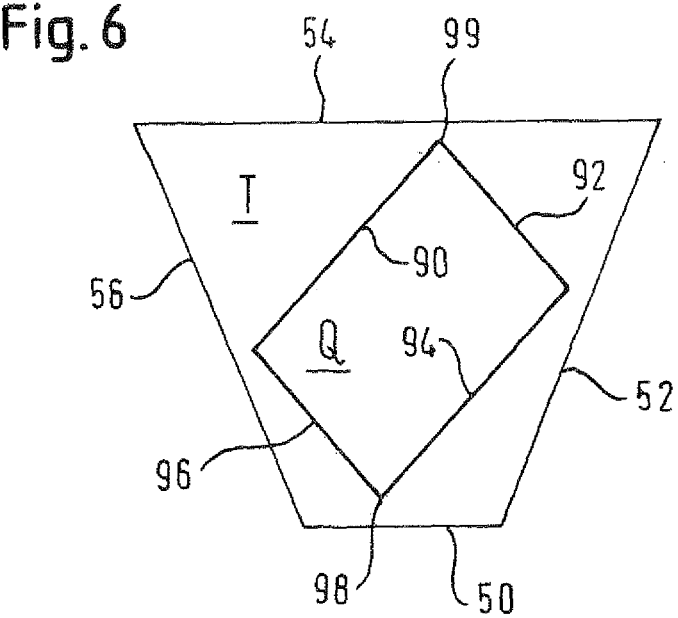

STENT

PRIORITY

This application is a continuation of U.S. patent application Ser. No. 14/045,603, filed Oct. 3, 2013, now U.S. Pat. No. 9,084,691, which is a division of U.S. patent application Ser. No. 12/514,177, filed May 8, 2009, now U.S. Pat. No. 8,551,156, which was filed as a U.S. national stage application under 35 USC §371 of International Application No. PCT/EP2007/062155, filed Nov. 9, 2007, which claims priority to U.K. Patent Application No. 0622465.3, filed Nov. 10, 2006, each of which is incorporated by reference in its entirety into this application.

FIELD OF THE INVENTION

This invention relates to a radially-expansible annular stent comprising a plurality of stenting turns around a lumen centered on a longitudinal axis, with adjacent turns being joined by connector struts, the stent annulus having a wall thickness that is related to the material of which it is formed.

BACKGROUND ART

In the field of radially expansible annular stents that are called upon, in use, to resist a radially inwardly directed force from surrounding bodily tissue, in order to maintain a bodily lumen patent, there is a contradictory design requirement. On the one hand, the stent must be strong enough to keep the lumen patent. On the other hand, the stent prosthesis must be flexible enough to accommodate movement of surrounding bodily tissue.

There are two archetypal stent forms. One of them has a stack of closed loop stenting rings, the length direction of the stent being along the length of the longitudinal axis of the annulus of the stent. The other archetype is the helical stent, in which the pattern of struts in the stent matrix performs a spiral path around the longitudinal axis, to create an annulus from one end of the stent to the other. Typically, each of the stenting loops is composed of closed periphery repeating unit cells. See EP-A-481365, FIG. 2. Typically, there are connector struts present, periodically through the annular matrix, to set the longitudinal spacing between adjacent stenting loops. See WO94/17754.

Such a stent is typically made from a seamless straight tubular workpiece so that its disposition, at rest, and relaxed, is that of a tubular cylindrical annulus. Typically, after implantation in the body, it is called upon to conform to an arcuate configuration of the bodily lumen in which it is placed. Such a change of shape necessitates the occurrence of strain within the matrix. That strain might not be homogeneously distributed throughout the matrix. Important for flexibility of the stent, after placement in the body, is a capacity for tolerating enough strain to give the stent, as such, enough flexibility to move with the body.

Another aspect of flexibility that is desirable when placing a stent is "radial conformability" by which is meant the ease with which succeeding turns of the stent can take or, after placement in tissue, different diameters clearly, when the struts connecting adjacent stenting rings have enhanced flexibility, an increase of radial conformability is in prospect.

Closed periphery unit cells of the stenting matrix are inherently rather well-adapted to provide the required resistance to the radially inwardly pressing force of the bodily tissue. In consequence, it is desirable for any connectors of unit cells, within the matrix, to deliver at least a substantial portion of the strain needed to allow the stent matrix to move with the body. Such flexibility in the connector links is not detrimental to the capability of the stenting loops to push the bodily tissue radially outwardly. For this reason, current stent designs often exhibit unit cells with simple straight strut peripheral portions, connected by connector struts that are not short and straight but long and thin. They are often meandering or arcuate or serpentine. There is discussed below, with reference to FIG. 1, showing an exemplary stent having connector struts of the serpentine kind This extra length provides the connectors with increased capacity to absorb strain and deliver flexibility to the stent, as such. However, building a stent annulus with convoluted or serpentine connectors adds to the complexity of manufacture and might not assist in meeting other government regulatory or quality control requirements.

It is an object of the present invention to ameliorate these difficulties.

SUMMARY OF THE INVENTION

According to the present invention, a stent as identified above is improved by arranging that, for the connector struts, the thickness of the struts is smaller than the ambient wall thickness of the stent.

Typically, stents are made from a seamless tubular workpiece of constant wall thickness. The description which follows will provide at least one way to produce a stent in accordance with the present invention from a seamless tubular workpiece of constant wall thickness.

Nickel-titanium shape memory alloy is a popular material from which to build self-expanding transluminally delivered bodily prostheses such as stents. Typically, they are made from the tubular workpiece by computer controlled laser cutting of slits in the workpiece, thereby to produce a matrix of struts. An attractive way to build stents in accordance with the present invention is by use of this laser cutting technique, known per se.

The conventional laser cutting process for making stents is with a laser beam arranged on a line that extends through the longitudinal axis of the stent annulus. However, the state of the art does include proposals, not only from the present applicant in WO 03/075797, WO 2006/010636 and WO 2006/010638 but also from others, such as Langhans et al in US 2006/0064153, to orient the laser beam on a line that does not pass through the longitudinal axis of the annulus. It is this step which is relied upon, in the presently preferred embodiment and best mode known to the inventor, as described in detail below. The concept can be conveniently designated "off-axis cutting".

As will be seen below, an attractive feature of using off-axis laser cutting of the connectors is that one can provide the connectors with a transverse cross-section that is in some way asymmetric in comparison with a "conventional" on-axis laser-cut strut. Thus, the connectors in accordance with the present invention may have a transverse cross-section that includes a luminal apex at the intersection of two straight lines, that apex being the closest approach of the connector to the longitudinal axis. It can also create a connector having a transverse cross-section that includes an abluminal apex at the intersection of two straight lines, the apex being the point on the connector furthest away from the longitudinal axis. Such cross-sections through the connector can reveal a lack of mirror symmetry about a plane that includes the length direction of the connector and the longitudinal axis of the stent annulus. In other words, we can have a connector in which the transverse cross-section reveals a luminal apex and an abluminal apex, and the line passing through both of these apices does not also pass through the longitudinal axis of the annulus of the stent.

As will be seen below, an attractive feature of the present invention is that it enables the creation of stent matrices that combine good radial force against bodily tissue with good flexibility both in the radially expanded and in the radially compressed dispositions in a design in which the connectors are simple, short, substantially straight struts.

The stiffness of a strut of a stent matrix is proportional to the strut width but, in relation to the strut thickness, it goes up with the cube of the thickness. A small reduction of strut thickness can therefore yield large gains in flexibility. This property is utilised in the present invention by providing connector struts with a smaller radial wall thickness than that of the stent annulus.

For a better understanding of the present invention and to show more clearly how the same may be carried into effect, reference will now be made, by way of example, to the accompanying drawings. These are incorporated herein and constitute part of this specification. They illustrate presently preferred embodiments of the invention and, together with the general description above, and the detailed description below, serve to explain the features of the invention.

BRIEF DESCRIPTION OF THE DRAWINGS

FIG. 3 shows the same stent under pressure from bodily tissue to bend it out of a straight line and FIG. 4 shows the same stent, strained, in response to changes of radially-inward force on the stent from surrounding bodily tissue, along the length direction of the stent.

FIG. 5 shows schematically in transverse cross-section three different stent matrix connector strut shapes; and FIG. 6 is a transverse cross-section like that of FIG. 5, but showing an "asymmetric" connector strut cross-section.

DETAILED DESCRIPTION

Figure 1:
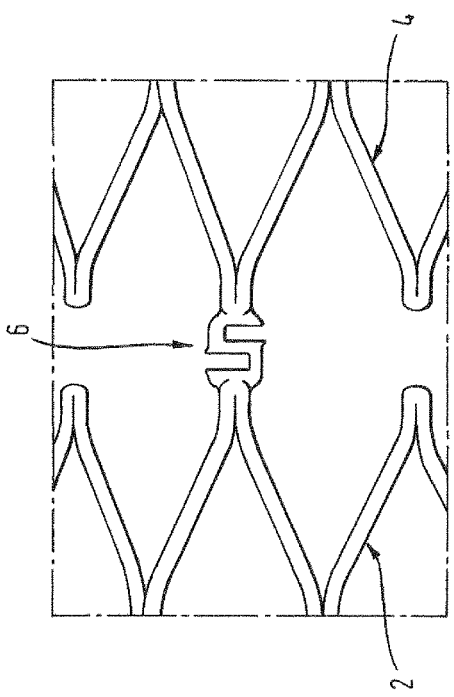
FIG. 1 is a view from the side of a stent, showing a small portion of the strut matrix of the stent that includes one connector strut.

Looking first at FIG. 1, the skilled reader will recognise portions of two adjacent zig-zag stenting rings 2, 4 and a single connector 6 of those two adjacent rings, central in the drawing Figure. That connector 6 shows a serpentine form, resembling the letter "S" lying on its side and with the base of the letter S contiguous with one of the two zig-zag stenting rings 2, 4 and the top of the letter S contiguous with the other of the two stenting rings. Self-evidently, the serpentine form of the connector 6 provides the stent matrix with capacity to undergo strain, somewhat additional to the capacity it would have if the serpentine connector 6 were to be replaced by a short straight link connecting the two zig-zag stenting rings 2, 4.

Figure 3:
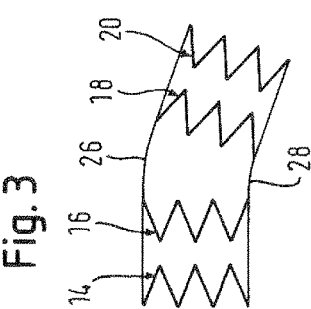
Figure 2:
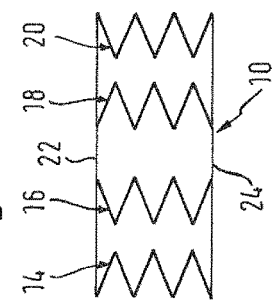

Turning to FIG. 2, we see diagrammatically a stent 10 composed of four zig-zag stenting rings 14, 16, 18 and 20 like the zig-zag rings shown in FIG. 1. The longitudinal straight lines 22 and 24 indicate the general form of the annulus of the stent. Now looking at FIG. 3, we can recognize that the annular stent matrix has undergone some strain, especially in the connector struts (not shown) between zig-zag ring 16 and zig-zag ring 18 and in the struts next to these connector portions. On the outside of the bend, at position 26, the tensile strain is accommodated by bending of the struts and, on the inside of the bend, at position 28, compressive stresses are likewise accommodated by bending of the struts. Ideally, the stent has sufficient flexibility to continue in the FIG. 3 disposition to deliver radially outwardly resistive force, even while it is bent into the arcuate shape of FIG. 3, away from the relatively more relaxed straight disposition of FIG. 2. One way to achieve good increases in bending flexibility without sacrificing much radial force delivered by the stent matrix would be to reduce the wall thickness of portions of the stenting ring struts immediately adjacent to the ring connector portions.

Figure 4:
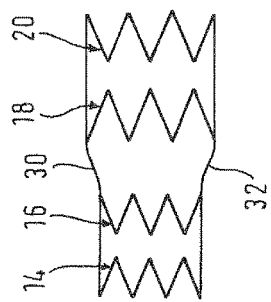
FIGS. 2, 3 and 4 each show diagrammatically a side view of a stent matrix with four zig-zag stenting rings, wherein FIG. 2 reveals the at-rest, relaxed disposition of the self-expanding stent.

FIG. 4 represents a situation in which the lumen in which the stent has been placed exerts a greater radially inward compressive force on zig-zag stenting rings 14 and 16 than on rings 18 and 20. In this situation, connector struts between zig-zag rings 16 and 18 suffer shear stresses which would bend them into a lazy S-shape such as is apparent from FIG. 4. Again, the connector portions of the stent matrix should exhibit enough flexibility in the zone between stenting ring 16 and 18 to permit the stent to take up a disposition as shown in FIG. 4, at positions 30 and 32. For this, one needs a significant degree of flexibility in the connectors linking stenting loops 16 and 18.

We turn now to FIGS. 5 and 6 to reveal how such flexibility can be provided.

Looking first at FIG. 5, a cross-section of a known connector strut T is shown with connector struts R, S of reduced cross-section overlaying it. The connector struts R and S are exemplary embodiments of the present invention. The reduced cross-section provides flexibility, as is explained below.

It is important to grasp that the drawing is schematic. A moment's thought from the reader will reveal that the trapezium T with sides 50, 52, 54 and 56 is not an accurate representation of a sector of a transverse section through an annular workpiece which is the precursor of the stent matrix. Sides 52 and 56 are correctly shown as straight lines, being in a plane that passes through the longitudinal axis of the annular workpiece, straight line 50 ought to be arcuate, being a portion of the luminal wall of the cylindrical lumen defined by the annular workpiece. Likewise, straight line 54 ought to be an arc of a circle with a somewhat larger radius than that of the luminal surface of the annular workpiece, to correspond with a portion of the abluminal surface of that workpiece.

However, showing sides 50 and 54 as straight lines serves the objective of clarity.

Readers will know that, when laser cutting an annular workpiece, with the beam of the laser on the axis of the annulus, planar flat surfaces, represented by lines 52 and 56, are the usual result.

However, once the possibility is taken up, to orient the laser beam "off-axis" so that the beam direction does not pass through the longitudinal axis of the annular workpiece and instead passes through a lumen of the workpiece, but offset from the longitudinal axis, then connector portions or strut cross-sections that are much smaller in area can readily be produced. FIG. 5 shows two examples, marked R and S, of such connector struts, in cross-section.

The connector strut section R is bounded by four cut-lines of the off-axis laser, namely, lines 60, 62, 64 and 66. This strut cross-section is truly a diamond rather than a sector of an annulus. Cross-section S is another possibility, with off-axis laser cut-lines 70, 72, 74 and 76.

In both cases, these connector strut cross-sections are symmetrical about a plane that extends through the longitudinal axis of the annulus of the workpiece, and the luminal apex 68 where cut-lines 64 and 66 intersect, and the abluminal apex 69 where cut-lines 60 and 62 intersect. In section S, the luminal apex is marked 78 and the abluminal apex is marked 80. In both cases, the luminal apex 68, 78 is further away from the longitudinal axis of the annulus than the luminal surface of the workpiece, and the abluminal apex 69, 80 is closer to the longitudinal axis than the abluminal surface of the annular workpiece. A reduction in the radial thickness has a particularly strong contribution to increasing flexibility. The flatter of the two connector struts marked S may, therefore, be more advantageous if flexibility is key.

Finally, turning to FIG. 6, we start with the same sector of the same annular workpiece, referenced with the same numbers, but show within it an asymmetric connector cross-section Q defined by laser cut-lines 90, 92, 94 and 96. Just as in FIG. 5, the intersection of cut-lines 94 and 96 produces a luminal apex 98 and the intersection of cut-lines 90 and 92 is at an abluminal apex 99. However, the plane that extends through these two apices 98 and 99, when extended radially inwardly, does not pass through the longitudinal axis of the annular workpiece.

One distinctive aspect of stent technology is how the strut matrix responds to expansion from a radially compact transluminal delivery disposition to a radially expanded deployed disposition. Reverting back to FIGS. 1 to 4, zig-zags in the compact disposition are linear struts separated by slits, with the slits and struts all lined up with the long axis of the stent whereas, in the deployed position, the zig-zag rings have opened out as shown in each of FIGS. 1 to 4. Interesting is how stresses are distributed during the process of expansion from the delivery to the deployed disposition. The reader will appreciate that use of an asymmetric connector form such as shown in FIG. 6 might yield a useful performance enhancement, in bringing peaks and valleys of zig-zag stenting rings into opposition, as opposed to a less attractive "peak-to-peak" design such as is apparent from FIG. 1. In FIG. 1, peaks (points of inflection) of adjacent zig-zag stenting rings are facing each other, with the consequence that these peaks are liable to impinge on each other when a deployed stent is forced into an arcuate configuration such as is evident from FIG. 3, on the inside of the bend, at position 28. By contrast, use of an asymmetric cross-section connector as shown in FIG. 6, offers the potential to "skew" the stresses undergone by the stent matrix, when expanding into the deployed configuration, to such an extent as to displace facing peaks of the zig-zag rings circumferentially with respect to each other, by just enough to carry each peak into a position between two facing peaks of the next adjacent zig-zag stenting ring, the better able to accommodate strain on the inside of a bend such as at position 28 in FIG. 3.

In some applications of stents, a high degree of plaque control is called for. Stents for the carotid artery is an example. Control is achieved by use of closed cell matrix structures, with a small mesh size and a relatively large number of connectors between adjacent stenting turns. An increasing number of connector struts reduces stent flexibility. The present invention offers a way to mitigate the flexibility problem without reducing the number of connector struts and thus can be particularly helpful in such applications.

The method of manufacture takes an appropriately sized tubular workpiece. Stenting turns are cut from this workpiece using a laser in the conventional way. That is, the laser beam follows a predetermined design pattern to form stenting struts to produce the stenting turns. In producing the stenting struts, the laser beam will be aimed to pass through the longitudinal axis of the tubular workpiece. The connector struts are cut by aiming the laser beam in an offset manner from the longitudinal axis of the workpiece. The cut is such that the radial wall thickness is reduced as compared to the radial wall thickness of the stenting struts. This may be achieved as in embodiments discussed above by creating a luminal or abluminal apex.

Readers of this specification are persons skilled in the art of stent design, who will find many other embodiments, once given the concept of the present invention in the description above. The description above is exemplary, but not limiting.

Where undulations are embodied in the form of zig-zag struts, the zig-zag struts may include a repeating pattern made of a unit of four generally linear members that extend oblique to the longitudinal axis to intersect each other at three apices spaced apart circumferentially and axially. Also, the prosthesis can utilize not only the circumferential bridges but also other bridge configurations in combination. Alternatively, the bridge directly connects a peak of one circumferential section to another peak of an adjacent circumferential section. In yet another alternative, the bridge may connect a peak of one circumferential section to a trough of an adjacent circumferential section. In a further alternative, the bridge can connect a trough of one circumferential section to a trough of an adjacent circumferential section. Moreover, the undulations can be wave-like in pattern. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern defined by the struts where the struts have substantially equal lengths or unequal lengths. And as used herein, the term "implantable prosthesis" is intended to cover not only a bare stent but also coated, covered, encapsulated, bio-resorbable stent or any portion of similar stents.

Bio-active agents can be added to the prosthesis (e.g., either by a coating or via a carrier medium such as resorbable polymers) for delivery to the host's vessel or duct. The bio-active agents may also be used to coat the entire stent. A material forming the stent or coupled to the stent may include one or more (a) non-genetic therapeutic agents, (b) genetic materials, (c) cells and combinations thereof with (d) other polymeric materials.

(a) Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

(b) Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins ("BMPrs"), B1VfiP-2, BMP-3, BMP-4, BMP-5, BMP-6 (Vgr-1), BMP-7 (0P-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

(c) Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

(d) Suitable polymer materials as a coating or the base material may include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL fibrin, collagen and derivatives thereof, polysaccharides such as celluloses, starches, dextrans, alginates and derivatives, hyaluronic acid, squalene emulsions. Polyacrylic acid, available as HYDROPLUS (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

While the invention has been described in terms of particular variations and illustrative figures, those of ordinary skill in the art will recognize that the invention is not limited to the variations or figures described. The method used in the present invention is not limited to the preferred method discussed above, as will be apparent from the claims. Further, the improved flexibility of the stents of the present invention may be achieved by methods other than the preferred one given above, as will be apparent to the skilled person. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of making a radially-expansible annular stent having a stent annulus that comprises a plurality of stenting turns around a lumen that is centered on a longitudinal axis, with adjacent turns being joined by connector struts, the stent annulus having a wall thickness that is related to an annulus material from which it is formed comprising:
   providing a seamless tubular work piece;
   cutting the seamless tubular work piece with a laser beam to form connector struts such that a thickness of the connector struts is cut smaller than that of the stent annulus and the annulus material from which it is formed, wherein the beam is aimed to not intersect the longitudinal axis in cutting luminally extending side walls of the connector struts;
   cutting the seamless tubular work piece with the beam to form stenting struts interspersed by points of inflection, the stenting turns being formed of the stenting struts, wherein the beam is aimed to intersect the longitudinal axis in cutting luminally extending side walls of the stenting struts,
wherein portions of the stenting turns that are immediately adjacent to the connector struts are formed to have a thickness smaller than that of the stent annulus.

2. The method of claim 1 wherein the connector struts comprise cut surfaces that intersect at a luminal apex radially further from the longitudinal axis than a luminal surface of the stent annulus.

3. The method of claim 2 wherein the connector struts comprise cut surfaces that intersect at an abluminal apex that is radially closer to the longitudinal axis than an abluminal surface of the stent annulus.

4. The method of claim 3 further comprising the step of cutting the cut surfaces intersecting at the luminal apex and the cut surfaces intersecting at the abluminal apex at different angles, such that a transverse cross-section through the connector struts reveals a lack of mirror symmetry about a plane that includes a length direction of the connector and the longitudinal axis of the stent annulus.

5. The method of claim 1 wherein the connector struts comprise cut surfaces that intersect at an abluminal apex that is radially closer to the longitudinal axis than an abluminal surface of the stent annulus.

* * * * *